Figure 1:
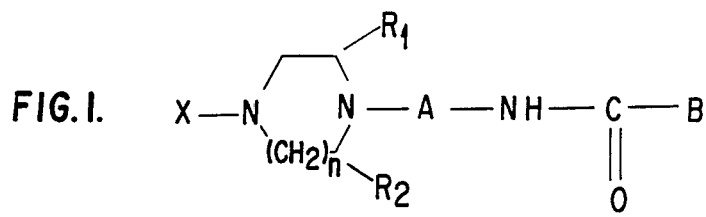
Figure 2:
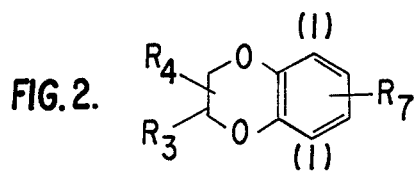
Figure 3:
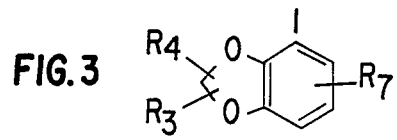
Figure 4:
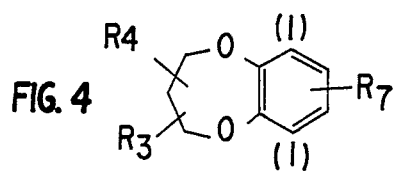
Figure 5:
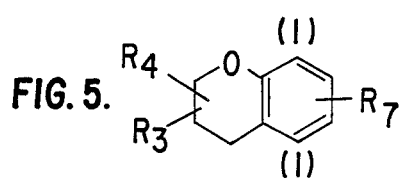
Figure 6:
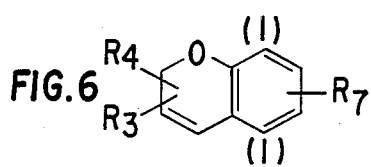
Figure 7:
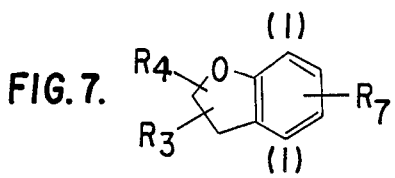
Figure 8:
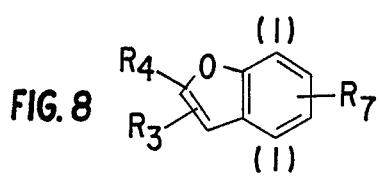
Figure 9:
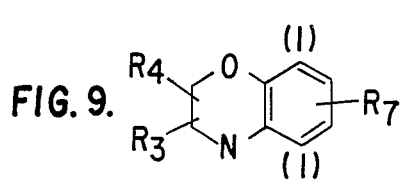
Figure 10:
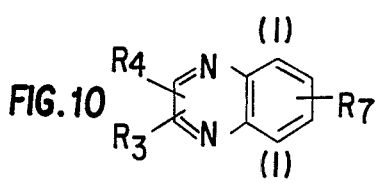
Figure 11:
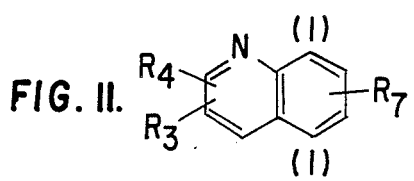
Figure 12:
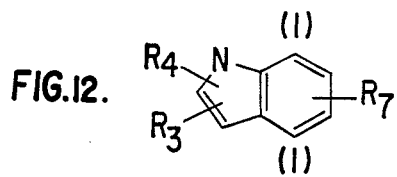
Figure 13:
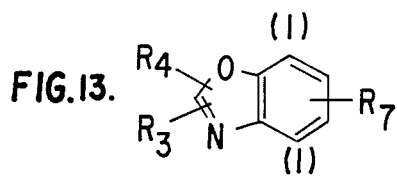
Figure 14:
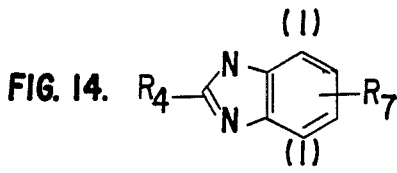
Figure 15:
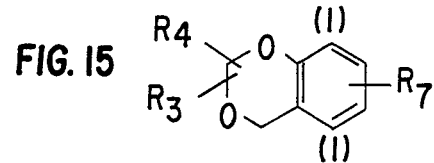
Figure 16:
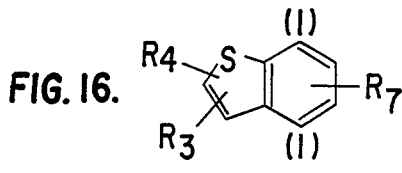
Figure 17:
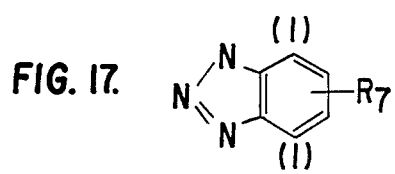
Figure 18:
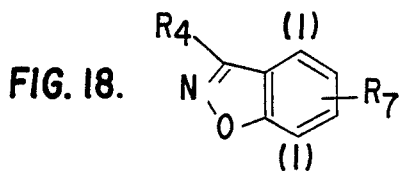
Figure 19:
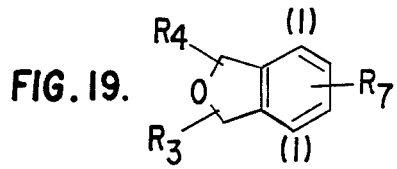
Figure 20:
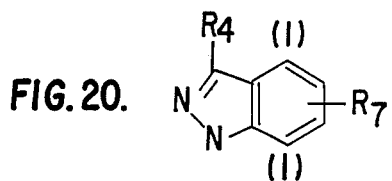
Figure 21:
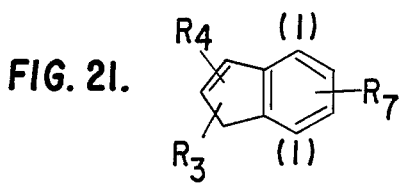
Figure 22:
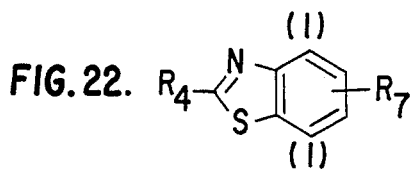
Figure 23:
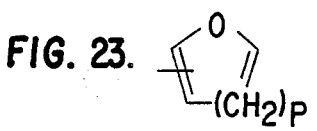
Figure 24:
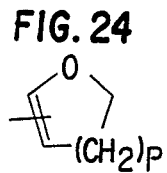
Figure 25:
Figure 26:
Figure 27:
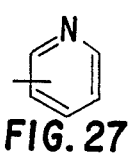
Figure 28:
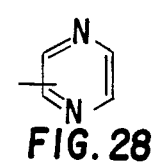
Figure 29:
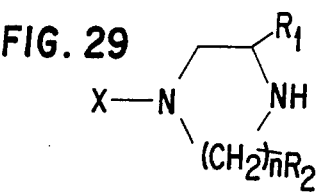
Figure 30:
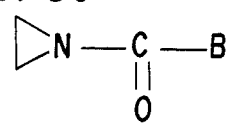
Figure 31:
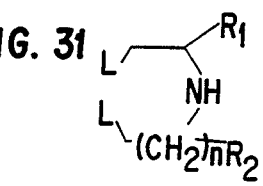
Figure 32:
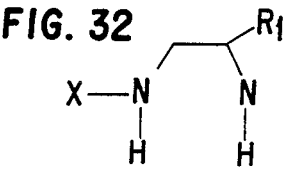
Figure 33:
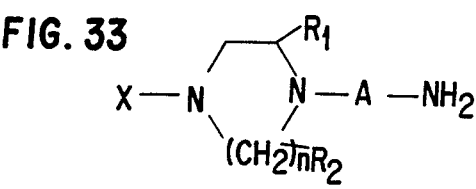
Figure 34:
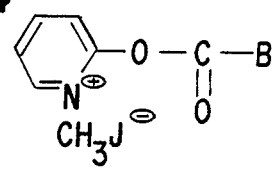
Figure 35:
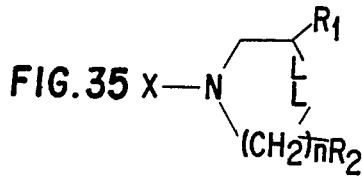
Figure 36:
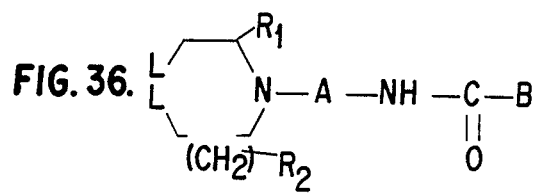
Figure 37:
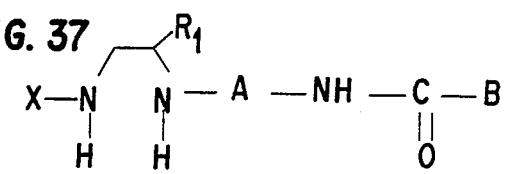
Figure 38:
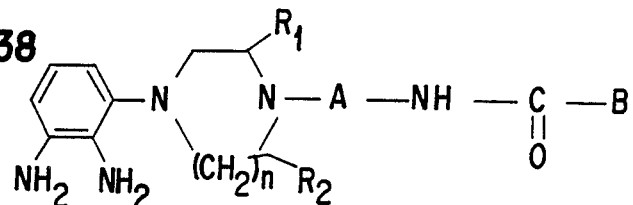
Figure 39:
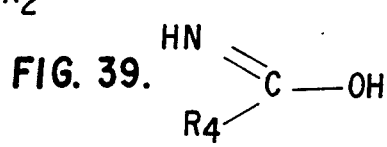

United States Patent [19]

Hartog et al.

[11] Patent Number: 4,833,142
[45] Date of Patent: May 23, 1989

[54] BLOOD-PRESSURE LOWERING 4-BICYCLIC-1-PIPERAZINYL-ALKYL AMIDES

[75] Inventors: Jan Hartog; Wouter Wouters; Lneke van Wijngaarden, all of Weesp, Netherlands

[73] Assignee: Duphar International Research B.V., Weesp, Netherlands

[21] Appl. No.: 118,005

[22] Filed: Nov. 9, 1987

Related U.S. Application Data

[63] Continuation-in-part of Ser. No. 660,054, Oct. 12, 1984, abandoned, which is a continuation-in-part of Ser. No. 805,809, Jun. 12, 1985, abandoned.

[30] Foreign Application Priority Data

Oct. 17, 1983 [NL] Netherlands ......................... 8303569

[51] Int. Cl.⁴ .................. A61K 31/495; C07D 413/04; C07D 405/04

[52] U.S. Cl. .................................... 514/254; 514/218; 514/230.5; 514/249; 514/255; 540/492; 544/105; 544/353; 544/355; 544/356; 544/357; 544/359; 544/360; 544/363; 544/364; 544/366; 544/368; 544/369; 544/370; 544/371; 544/372; 544/373; 544/376; 544/377; 544/379; 544/400

[58] Field of Search ............... 544/105, 353, 355, 356, 544/357, 359, 360, 363, 364, 366, 368, 369, 370, 371, 372, 373, 376, 377, 379, 400; 540/492; 514/254, 218, 230.5, 249, 255

[56] References Cited

FOREIGN PATENT DOCUMENTS 0048045 3/1982 European Pat. Off. ............ 544/379
0138280 4/1985 European Pat. Off. ............ 544/376
8201708 4/1982 Netherlands .

OTHER PUBLICATIONS

Hartog, et al., "Chemical Abstracts", vol. 103, 1985, col. 103:123520x.

*Primary Examiner*—Glennon H. Hollrah
*Assistant Examiner*—James H. Turnipseed
*Attorney, Agent, or Firm*—Stevens, Davis, Miller & Mosher

[57] ABSTRACT

Blood-pressure lowering compounds having a structure as shown in the accompanying formula sheets.

12 Claims, 3 Drawing Sheets

BLOOD-PRESSURE LOWERING 4-BICYCLIC-1-PIPERAZINYL-ALKYL AMIDES

This application is a continuation-in-part of our prior application Ser. No. 805,809, filed Dec. 6, 1985, and now abandoned, which in turn is a continuation-in-part of our prior application Ser. No. 660,054, filed Oct. 12, 1984, and now abandoned.

The invention relates to new bloodpressure lowering piperazine derivatives, to compositions which comprise these compounds as the active substance, and to the preparation of the new compounds.

It has been found that the group of compounds of the general formula 1 of the formula sheet and the salts thereof with pharmaceutically acceptable acids, wherein $R_1$ and $R_2$ independently of each other represent hydrogen or an alkyl group having 1-3 carbon atoms, n has the value 1 or 2, X is one of the groups of formulae 2-22, on the understanding that the groups of the formulae 2, 4, 5, 6, 9, 10, 11 and 15 can be linked on position 5 or 8, and the groups of formulae 7, 8, 12, 13, 14 and 16-22 can be linked on position 4 or 7 to the nitrogen atom of the piperazine group, and in which groups $R_3$ is hydrogen or straight or branched alkyl having 1-3 carbon atoms, $R_4$ is hydrogen, halogen, alkyl having 1-3 carbon atoms, methylene, ethylidene or vinyl an optionally branched hydroxyalkyl group having 1-3 carbon atoms, which may optionally be etherified or esterified, or an alkyl carbonyl group having 1-3 carbon atoms in the straight or branched alkyl group, an oxo group or an optionally substituted phenyl group, and $R_7$ is a hydrogen or fluoro atom, A is a straight or branched alkyl group B is an aryl group or a heteroaryl group optionally substituted by one or more substituents, a straight or branched alkyl group or a saturated or partly unsaturated cycloalkyl group having 4-10 carbon atoms, have good blood-pressure lowering properties.

The group B is preferably phenyl or a group of the formulae 23-28, wherein p has the value 1 or 2. Examples of suitable subsituents of group B are halogen, trifluoromethyl, nitrile, nitro, alkoxy having 1-3 carbon atoms, hydroxy, esterified hydroxy, and alkyl having 1 or 2 carbon atoms. A cycloalkyl group B may also be a polycycloalkyl group, for example the adamantyl group.

When $R_4$ is an esterified hydroxyalkyl group, the ester group preferably has the formula

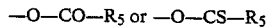

—O—CO—$R_5$ or —O—CS—$R_5$ wherein $R_5$ is alkyl, aralkyl, aryl, heteroaralkyl, heteroaryl, wherein alkyl may be branched or unbranched and the (hetero)aryl part may or may not be substituted, or $R_5$ is alkoxy, heteroaralkoxy, or a dialkylamino group in which the two alkyl grouls can form a heterocyclic ring with the nitrogen atom.

On the basis of their properties the compounds of formula 1 are to be preferred, wherein n=1, $R_1=R_2=H$; B has the above-mentioned meaning, A is a straight or branched alkyl group containing 2-10 carbon atoms, and X is the group of formula 2, wherein $R_3$ and $R_7$ are hydrogen, and $R_4$ is hydrogen, hydroxymethyl or esterified hydroxymethyl in position 2 of the benzodioxane ring. Compounds which are to be preferred in particular are:

1. racemate and (+)-enantiomer of 4-fluoro-N-[2-{4-[5-(2-hydroxymethyl-1,4-benzodioxanyl)]-1-piperazinyl}ethyl]-benzamide;
2. 4-fluoro-N-[2-{4-[5-(2,2-dimethyl-1-oxopropyloxymethyl)-1,4-benzodioxanyl]]-1-piperazinyl}ethyl]-benzamide;
3. N-[2-methyl-2-{4-[5-(1,4-benzodioxanyl)]-1-piperazinyl}-ethyl]cyclohexane carbonamide
4. (+)-4-fluoro-N-[3-[4-[5-(2-hydroxymethyl-1,4-benzodioxanyl)]1-piperazinyl]propyl]benzamide
5. (+)-4-fluoro-N-[4-[4-[5-(2-hydroxymethyl-1,4-benzodioxanyl)]1-piperazinyl]butyl]benzamide
6. 4-fluoro-N-[3-[4-[7-(2-hydroxybenzoxazolyl)]-1-piperazinyl]propyl]benzamide
7. 4-fluoro-N-[3-[4-(4-benzotriazolyl)-1-piperazinyl]-propyl]benzamide and the salts of these compounds.

The invention also includes the so-called prodrugs and acid addition salts of the compounds of formula 1. Prodrugs are to be understood to mean derivatives from which, after administration, an active compound of formula 1 is released.

Suitable acids with which the compounds according to the invention can form pharmaceutically acceptable salts are, for example, hydrochloric acid, sulfuric acid, phosphoric acid, nitric acid, organic acids such as citric acid, fumaric acid, tartaric acid, acetic acid, maleic acid, benzoic acid, p-toluenesulfonic acid, methane sulfonic acid, and the like.

When the compounds according to the invention comprise one or more optically active carbon atoms, both the racemates and the individual enantiomers belong to the invention.

The compounds according to the invention are useful as agents for circulatory diseases. They can be used as blood-pressure lowering agents. In general the compounds have a long duration of action. The compounds have no or substantially no sedating properties and substantially no influence on the heart frequency.

The blood-pressure lowering activity of the compounds according to the invention was measured in at least one of the two following test models.

A. Blood-pressure measurement in the normotensive anaesthetized cat.

In this model the hypotension is measured in normotensive cats which are anaesthetized with 35 mg/kg (i.p.) of pentobarbital. The animals are provided with an arterial canule in order to be able to record the blood pressure directly and continuously. The compound to be tested, dissolved in a physiological saline solution or in another suitable carrier, is administered intravenously in increasing doses. The maximum effect on the mean blood pressure, the heart frequency which is derived from the blood pressure pulse, and the duration of these effects are measured.

The effectiveness of the tested compound is represented as $ED_{80}$, i.e. the dosis determined by extrapolation at which 20% decrease of the mean blood pressure occurs.

B Blood pressure measurement in the spontaneoulsy hypertensive rat (SHR).

Spontaneously hypertensive rats are used in this model. The animals are provided with an arterial canule while under a light ether anaesthesia. At least two days later the animals are used for the blood pressure test.

The mean arterial blood pressure is measured continuously. The compound to be tested is suspended in tragacanth and administered through a stomach tube. The maximum decrease of the blood pressure and the duration of the effect are measured The $ED_{80}$ is calculated from the found values for the various dosages.

In model A the compounds according to the invention have an $ED_{80}$ which is between $10^{-4}$ and 1 mg/kg and/or in model B they have an $ED_{80}$ between about 1 and 25 mg/kg.

The compounds can be brought in a form of administration which is suitable for human application as an blood-pressure lowering agent, i.e. they may be formulated to compositions which are suitable for this purpose and can preferably be administered orally.

The new compounds according to the invention can be obtained in a manner known for the synthesis of analogous compounds.

The compound can be obtained, for example, by reaction of a compound of formula 29 with a compound of the formula

in which formulae $R_1$, $R_2$, n, X, A, and B have the above-mentioned meanings, and L is a so-called "leaving" group, preferably chlorine, bromine or tosylate.

This reaction may be carried out both with and without an inert organic solvent. Suitable organic solvents are, for example, methyl ethyl ketone, dimethyl formamide, tetrahydrofuran, petroleum ether, alcohol and acetonitrile. In order to bind the releasing acid, an acid binder, for example $NaHCO_3$ or $K_2CO_3$ may be used. The reaction temperature is usually between room temperature and the boiling-point of the solvent used.

A modification of this method may be used for the preparation of compounds according to the invention, in which A is the ethylene group, by reaction of a compound of formula 29 with a compound of formula 30 of the formula sheet. In these formulae $R_1$, $R_2$, X and B have the above-mentioned meanings. The reaction components are heated at 100° C. for 1–6 hours, preferably without a solvent. However, it is also possible to carry out the reaction in an inert solvent, for example acetone, methyl ethyl ketone or toluene, at a temperature between room temperature and the boiling-point of the solvent used.

The starting substances of formula 29 in which $R_1$, $R_2$, n, and X have the meanings mentioned above, which are used for these methods of preparation are new compounds, except for the compounds wherein $R_1$ and $R_2$ are hydrogen, n has the value 1 or 2 and X is 4-(or 7) benzimidazolyl optionally substituted in postion 2 with alkyl or phenyl, or X is 4-(or 7) indolyl or 4-(or 7) benzotriazolyl or 8-quinolinyl. These compounds are known from Netherlands patent application No. 82.01708 and Ber. 74B, (1941), page 1661–1663 respectively. Since these new compounds are particularly suitable as starting materials for the preparation of compounds in which the hydrogen atom at the nitrogen atom of the piperazine ring is replaced by a functional group, the invention also relates to the new compounds of formula 29 and to the preparation thereof according to methods known for the synthesis of analogous compounds.

Methods which are suitable for the preparation of the intermediate products of formula 29 are described, for example, in Netherlands Patent Application No. 80.05133 and 82.01708:

(a) Reaction of a compound $X$-$NH_2$ with a compound of formula 31 of the formula sheet. In these formulae X, $R_1$, $R_2$, and n have the above-mentioned meanings, and L is a "leaving" group, for example halogen, preferably chlorine.

(b) Reaction of a compound L-$(CH_2)_n$—$CH_2$—L with a compound of formula 32 of the formula sheet, in which X, $R_1$, n and L have the above-mentioned meanings.

The methods (a) and (b) are also suitable for the preparation of final products according to the invention. By carrying out the reactions with a compound of formula 31 or 32 in which the secundary and primary nitrogen atom, respectively, is substituted with a group - A - NHCO - B, i.e. a compound of the formula 36 and 37 respectively, a compound of formula 1 can be directly obtained.

A few other methods, known inter alia from Netherlands Patent Application 80.05133, which may be used for the preparation of the compounds according to the invention are:

(a) Reaction of a compound of formula 33 with
 (1) an ester of an acid of the formula HOOC-B, or
 (2) an acid chloride of the formula Cl—CO—B, or
 (3) a mixed anhydride of the formula $R_6$—O—CO—O—CO—B, or
 (4) a so-called Mukayama ester of formula 34 of the formula sheet.

In these formulae X, A, n, $R_1$, $R_2$ and B have the above-mentioned meanings, and $R_6$ is preferably an alkyl group having 1–3 carbon atoms.

(b) Reaction of a compound of formula 35 with a compound of the formula $NH_2$—A—NH—CO—B wherein the symbols have the meanings given hereinbefore.

Furthermore the compounds of the formula 1, wherein X is a group of the formula 14 or 17 an the remaining symbols have the above given meanings can be obtained by reacting a compound of the formula 38 of the formula-sheet:

a. with an ester of an imino acid of the formula 39 or
 b. with a carboxylic acid of the formula $R_4$—COOH, or
 c. with a reactive carbonyl compound, preferably N,N'-carbonyldiimidazole, or
 d. with an alkali metal nitrite in an aqueous medium, preferably sodium nitrite, in the presence of hydrochloric acid.

Furthermore, the compounds in which $R_4$ is a hydroxy alkyl group can be obtained by hydrolysis of the corresponding compound in which $R_4$ is an esterified hydroxy alkyl group.

Also, conversely, compounds in which $R_4$ is a hydroxy alkylgroup can be converted into final products in which $R_4$ is an esterified hydroxy alkyl group by esterification in a manner known per se.

Finally, the desired final products of formula 1 in which the symbols have the meanings given hereinbefore, can be obtained in that, as the last reaction step, one or more protective groups used for the protection of functional groups are removed or converted by means of methods usual for this purpose.

The individual enantiomers of compounds of formula 1 can be obtained according to methods known per se, for example, by starting from optically active intermediate products, or by resolving the racemic end products into the enantiomers by means of the methods usual for this purpose.

The invention will now be described in greater detail with reference to the following specific examples.

EXAMPLE I

4-Fluoro-N-[2-[4-{5-(2-ethoxymethyl-1,4-benzodioxanyl)}-1-piperazinyl]ethyl]benzamide HCl.

9.82 Mmol (2,73 g) of 1-{5-(2-ethoxymethyl-1,4-benzodioxanyl)}(piperazine were dissolved in 30 ml of acetone. A solution of 9.82 mmol (1.62 g) of 1-(4-fluorobenzoyl)aziridine in 10 ml of acetone was added at once and the mixture was refluxed for 2 hours. The reaction mixture was evaporated to dryness in vacuo, after which the residue was heated in vacuo (15 mm Hg) at 85° C. for 3 hours. The reaction mixture was then dissolved in 10 ml of ethanol and 1 equivalent of hydrochloric acid in ethanol was added. After diluting with 5 ml of ether, the title compound was obtained having a melting-point 197°–198° C.

The following compounds were prepared in an analogous manner from the said starting compounds:

2. 4-fluoro-N-[2-[4-{5-(2-benzoyloxymethyl-1,4-benzodioxanyl)}-1-piperazinyl]ethyl]benzamide HCl; meltingpoint 212°–214° C. (ethanol-ether 9:1), from 1- 5-(2-benzoyloxymethyl-1,4-benzodioxanyl) piperazine and 1- (4-fluorobenzoyl)aziridine;

3. 4-fluoro-N-[2-[4- 5-(3-benzoyloxymethyl-1,4-benzodioxanyl)-1-piperazinyl]ethyl]benzamide HCl; meltingpoint 159°–160.5° C. (ethanol-ether 3:1), from 1-{5-(3-benzoyloxymethyl-1-1,4-benzodioxanyl)} piperazine and 1-(4-fluorobenzoyl)aziridine;

4. 4-fluoro-N-[2-[4-{5-(2-benzoyloxyethyl-1,4-benzodioxanyl)}-1-piperazinyl]ethyl]benzamide HCl; meltingpoint 172°–173° C. (ethanol-ether 4:1), from 1-{5-(2-benzoyloxyethyl-1,4-benzodioxanyl)}piperazine and 1-(4-fluorobenzoyl)aziridine;

5. N-[2-[4-{5-(2,3-dihydro-1,4-benzoxazinyl}-1-piperazinyl]ethyl]cyclohexane carbonamide HCl (oil), from 1-{(5-(2,3-dihydro-1,4-benzoxazinyl)} piperazine and 1-(cyclohexane carbonyl)aziridine;

6. 4-fluoro-N-[2-{4-(8-quinolinyl)1-piperazinyl}ethyl]benzamide HCl; melting-point 243°–245° C. (decomposition) (ethylacetate-ethanol 9:1), from 1-(8-quinolinyl)-piperazine and 1-(4-fluorobenzoyl)aziridine:

7. 4-fluoro-N-[2-[4-{5-(2-(2,2-dimethyl-1-oxopropyloxymethyl)-1,4-benzodioxanyl)}-1-piperazinyl]ethyl]benzamide HCl; melting point 199.5°–201° C. (ethyl acetateethanol 1:2) from 1-[5-{2-(2,2-dimethyl-1-oxopropyloxymethyl)-1,4-benzodioxany }piperazine and 1-(4-fluorobenzoyl)aziridine;

8. (+)4-fluoro-N-[2-[4-{5-(2-(2,2-dimethyl-1-oxopropyloxymethyl) 1,4-benzodioxanyl)}-1-piperazinyl]ethyl]benzamide HCl; melting-point 200°–201° C. (ethanol), from (+)- 1-[5-{2-(2,2-dimethyl-1-oxopropyloxymethyl)-1,4-benzodioxanyl}]piperazine and 1-(4-fluorobenzoyl)aziridine.

In a corresponding manner the following compounds were isolated as the free base and crystallized.

9. 4-fluoro-N-[2-[4-{5-(1,4-benzodioxanyl}-1-piperazinyl]ethyl]benzamide; melting-point 170°–171° C. (ethyl acetate), from 1-{5-(1,4-benzodioxanyl)}piperazine and 1-(4-fluorobenzoyl)aziridine;

10. N-[2-[4{5-(1,4-benzodioxanyl)}-1-piperazinyl]ethyl]cyclohexane carbonamide; melting-point 154.5°–156° C. (methyl ethyl ketone), from 1-{5-(1,4-benzodioxanyl}piperazine and 1-(4-fluorobenzoyl)aziridine;

11. 4-fluoro-N-[2-[4- 5-(2-methyl-1,4-benzodioxanyl) -1-piperazinyl]ethyl]benzamide; melting-point 202°–206° C. (toluene-petroleum ether 3:1), from 1-5-(2-methyl-1,4-benzodioxanyl) piperazine and 1-(4-fluorobenzoyl)aziridine;

12. 4-fluoro-N-[2-[4-{5-(3-methyl-1,4-benzodioxanyl)}-1-piperazinyl]ethyl]benzamide; melting-point 169°–169, 5° C. (ethyl acetate), from 1-{5-(3-methyl-1,4-benzodioxanyl)}piperazine and 1-(4-fluorobenzoyl)aziridine;

13. 4-fluoro-N-[2-[4-{8-(2,3-dihydrobenzopyranyl)}-1-piperazinyl]ethyl]benzamide; melting-point 157°–158° C. (ethyl acetate-ether 4:1) from 1-{8-(2,3-dihydro-benzopyranyl)}piperazine and 1-(4-fluorobenzoyl)aziridine;

14. 4-chloro-N-[2-[4-{8-(2,3-dihydrobenzopyranyl)}-1-piperazinyl]ethyl]benzamide; melting-point 172°–173,5° C. (ethyl acetate) from 1-){8-(2,3-dihydrobenzopyranyl)}-piperazine and 1-(4-chlorobenzoyl)aziridine;

15. N-[2-[4-{8-(2,3-dihydrobenzopyranyl)}-1-piperazinyl]ethyl]cyclohexane carbonamide; melting-point 164°–166° C. (ethyl acetate) from 1-{8-(2,3-dihydrobenzopyranyl)}-piperazine and 1-(cyclohexane carbonyl)aziridine;

16. 4-fluoro-[2-[4-{8-(2H-1-benzopyranyl)}-1-piperazinyl]-ethyl]benzamide; melting-point 131.5°–133.5° C. (ethyl acetate-petroleum ether 9:1), from 1-{8-(2H-1-benzopyranyl)}piperazine and 1-(4-fluorobenzoyl)aziridine;

17. 4-fluoro-[2-[4-{8-(2,3-dihydro-4H-1-benzopyran-4-one)}-1-piperazinyl]ethyl]benzamide; melting point 175.5°–177.5° C. (ethyl acetate-petroleum ether 9:1), from 1-{8-(2,3-dihydro-4H-1-benzopyran-4-one)}piperazine and 1-(4-fluorobenzoyl)aziridine;

18. 4-fluoro-N-[2-{4-(7-benzofuranyl)-1-piperazinyl}ethyl]-benzamide; melting-point 150.5°–152° C. (ethyl acetate) from 1-(7-benzofuranyl)piperazine and 1-(4-fluorobenzoyl)aziridine;

19. 4-fluoro-N-[2-{4-(1,3-benzodioxolyl)-1-piperazinyl}-ethyl]benzamide; melting-point 179.5°–182° C. (ethanolwater 9:1) from 1-{4-(1,3-benzodioxolyl)}piperazine and 1-(4-fluorobenzoyl)aziridine;

20. 4-fluoro-N-[2-[4-{6-(3,4-dihydro-(2H)-1,5-benzodioxepinyl)}1-piperazinyl]ethyl]benzamide; melting-point 176°–177° C. (ethyl acetate) from 1-{6-(3,4-dihydro-(2H)--1,5-benzodioxepinyl)}piperazine and 1-(4-fluorobenzoyl)aziridine;

21. 4-fluoro-N-[2-{4-(5-quinoxalyl)-1-piperazinyl}ethyl]benzamide; melting-point 170.5°–172° C. (ethyl acetate), from 1-(5-quinoxalyl)piperazine and 1-(4-fluorobenzoyl)aziridine;

22. 4-fluoro-N-[2-[4-{8-(2,3-dihydro-1,4-benzoxazinyl)}-1-piperazinyl]ethyl]benzamide; melting-point 148°–150°,5° C. (ethanol) from 1-{8-(2,3-dihydro-1,4-benzoxazinyl}piperazine and 1-(4-fluorobenzoyl)aziridine;

23. 4-fluoro-N-[2-[4-{7-(2-phenylbenzoxazolyl)}-1-piperazinyl]ethyl]benzamide; melting point 214°–216° C. (methyl ethyl ketone) from 1-{7-(2-phenylbenzoxazolyl}piperazine and 1-(4-fluorobenzoyl)aziridine;

24. 4-fluoro-N-[2-[4-{4-(3-methyl-1,2-benzisoxazolyl)}-1-piperazinyl]ethyl]benzamide; melting-point 172°–174,5° C. (toluene) from 1-{4-(3-methyl-1,2-benzisoxazolyl)}piperazine and 1-(4-fluorobenzoyl)aziridine;

25. 4-fluoro-N-[2-{4-(7-indolyl)-1-piperazinyl}ethyl]-benzamide; melting-point 138°-140° C. (methylene chloride/petroleum ether) from 1-(7-indolyl)piperazine and 1-(4-fluorobenzoyl)aziridine; methyl]ben 26. 4-fluoro-N-[2-{4-(4-indolyl)-1-piperazinyl}ethyl]-benzamide; melting-point 123°-125° C. (methylene chloride/petroleum ether) from 1-(4-indolyl)piperazine and 1-(4-fluorobenzoyl)aziridine.

EXAMPLE II

N-[2-[4-{7-(2,3-dihydrobenzofuranyl}-1-piperazinyl]ethyl]benzamide HCl.

11.18 Mmol (2.28 g) of 1-[7-(2,3-dihydrobenzofuranyl)]piperazine and 11.18 mmol (2.05 g) of N-(2-chloroethyl)benzamide were dissolved in 5 ml of acetonitrile and the mixture was heated at 60° C. for 31 hours. The reaction mixture was evaporated to dryness in vacuo and the residue was taken up in 20 ml of 2 N hydrochloric acid and extracted with 3×20 ml of methylene chloride. The organic layer, after washing with 40 ml of water, was evaporated to dryness in vacuo. The residue was dissolved in ethanol (20 ml), after which 1 equivalent of hydrochloric acid in ethanol was added. After diluting with 4 ml of ether the title compound was obtained with a melting-point of 235°-235.5° C.

EXAMPLE III 4-fluoro-N-[2-[4-{7-(2,3-dihydrobenzofuranyl)}-1-piperazinyl]ethyl]benzamide, HCl.

4.49 Mmol (1.11 g) of 2-[4-{7-(2,3-dihydrobenzofuranyl)}-1-piperazinyl]ethylamine were dissolved in 20 ml of methylene chloride. A solution of 4.5 mmol (0.71 g) of 4-fluorobenzoyl chloride in 10 ml of methylene chloride was added dropwise, while stirring. After leaving to stand at room temperature for 16 hours the reaction mixture was evaporated to dryness under reduced pressure and the residue was crystallized from a mixture of 40 ml of ethanol and 10 ml of ether, after which the title compound was obtained with a melting-point of 223.5°-224.5° C.

The following compounds were prepared from the said starting substances in an analogous manner:

2. 4-cyano-N-[2-[4-{7-(2,3-dihydrobenzofuranyl)}-1-piperazinyl]ethyl]benzamide HCl, melting-point 252°-253.5° C. (ethanol) from 2-[4-{7-(2,3-dihydrobenzofuranyl)}-1-piperazinyl]ethylamine and 4-cyanobenzoyl chloride;

3. 4-nitro-N-[2-[4-{7-(2,3-dihydrobenzofuranyl)}-1-piperazinyl]ethyl]benzamide HCl, melting point 248°-249° C. (ethanol-water 9:1) from 2-[4-{7-(2,3-dihydrobenzofuranyl)}-1-piperazinyl]ethylamine and 4-nitrobenzoyl chloride;

4. 2,4-difluoro-N-[2-methyl-2-[4-{5-(1,4-benzodioxanyl),}-1-piperazinyl]ethyl]benzamide HCl, melting point 203°-205° C. (methyl ethyl ketone) from 2-methyl-2-[4-{5-(1,4-benzodioxanyl}-1-piperazinyl]ethylamine and 2,4-difluorobenzoyl chloride.

5. 4-fluoro-N-[2-methyl-2-[4-{5-(1,4-benzodioxanyl)}-1-piperazinyl]ethyl]benzamide HCl, melting point 227°-228.5° C. (methyl ethyl ketone) from 2-methyl-2-[4-{5-(1,4-benzodioxanyl)}-1-piperazinyl]ethylamine and 4-fluorobenzoyl chloride.

6. N-[2-methyl-2-[4-{5-(1,4-benzodioxanyl)}-1-piperazinyl]ethyl]cyclohexane carbonamide, melting-point 200.5°-202° C. (methyl ethyl ketone) from 2-methyl-2-[4-{5-(1,4-benzodioxanyl)}-1-piperazinyl]ethylamine and cyclohexane carbonyl chloride.

7. (+)-4-fluoro-N-[3-[4-[5-(2-hydroxymethyl-1,4-benzodioxanyl)]-1-piperazinyl]propyl]benzamide dihydrochloride (melting point 183°-185° C., ethanol/ether 1:1) from (+)-3-[4-[5-(2-hydroxymethyl-1,4-benzodioxanyl)]-1-piperazinyl]propylamine and 4-fluorobenzoyl chloride.

8. (+)-4-fluoro-N-[4-[4-[5-(2-hydroxymethyl-1,4-benzodioxanyl)]-1-piperazinyl]butyl]benzamide dihydrochloride (melting point 206°-209° C., ethanol/ether 1:1) from (+)-4-[4-[5-(2-hydroxymethyl-1,4-benzodioxanyl)]-1-piperazinyl]butylamine and 4-fluorobenzoyl chloride.

9. 4-fluoro-N-[3-[4-[7-(2-hydroxybenzoxazolyl)]-1-piperazinyl]propyl]benzamide, (melting point 215°-218° C., ethanol) from 3-[4-[7-(2-hydroxybenzoxazolyl)]-1-piperazinyl]propylamine and 4-fluorobenzoyl chloride.

10. (+)-4-fluoro-N-[5-[4-[5-(2-hydroxymethyl-1,4-benzodioxanyl)]-1-piperazinyl]pentyl]benzamide dihydrochloride (melting point 183°-187° C., ethanol/ether 3:1) from (+)-5-[4-[5-(2-hydroxymethyl-1,4-benzodioxanyl)]-1-piperazinyl]pentylamine and 4-fluorobenzoyl chloride.

11. (+)-4-fluoro-N-[7-[4-[5-(2-hydroxymethyl-1,4-benzodioxanyl)]-1-piperazinyl]heptyl]benzamide dihydrochloride (melting point 174°-182° C., decomposition; ethanol/ethylacetate 1:1) from (+)-7-[4-[5-(2-hydroxymethyl-1,4-benzodioxanyl)]-1-piperazinyl]heptylamine and 4-fluorobenzoyl chloride.

EXAMPLE IV 4-fluoro-N-[2-[4-{5-(2-benzoyloxymethyl-1,4-benzodioxanyl)}-1-piperazinyl]ethyl]benzamide HCl.

1.12 mmol (0.55 g) of 4-fluoro-N-[N'-[N''-{5-(2-benzoyloxymethyl-1,4-benzodioxanyl)}-2-aminoethyl]-2-aminoethyl]benzamide were dissolved in 3 ml of dioxane and a solution of 0.22 mmol (0.042 g) of 1,2-dibromoethane in 1 ml of dioxane was added. The mixture was heated at 120° C. for 68 hours. The reaction mixture was evaporated to dryness in vacuo and the residue, dissolved in 10 ml of methylene chloride, was washed with 5 ml of 1 N sodium hydroxide and then with water. The organic layer was dried on magnesium sulfate and evaporated to dryness under reduced pressure. The residue was chromatographed over silicagel with methylene chloride-methanol (97/3) as an eluent. The resulting base was dissolved in ethanol and after the addition of 1 equivalent of hydrochloric acid in ethanol, the solution was diluted with ether, after which the title compound was isolated with a melting-point of 210°-211° C.

EXAMPLE V

N-[2-4-{7-(2,3-dihydrobenzofuranyl}-1-piperazinyl]ethyl]-benzamide HCl.

10 Mmol (1.35 g) of 7-amino-(2,3-dihydro)benzofuran, 0.1 g of sodium iodide and 5 mmol (0.69 g) of potassium carbonate were added successively to a solution of 10 mmol (3.25 g) of N-[2-{N',N'-bis(2-chloroethyl)-}aminoethyl]benzamide in 6 ml of isopropanol. This mixture was heated at 60° C. for 17 hours and then evaporated to dryness under reduced pressure. The residue was taken up in 50 ml of water and this solution was washed with 3×100 ml of ether. The aqueous layer, after the addition of 5 ml of 2N potassium hydroxide, was extracted with 2×75 ml of methylene chloride. The extract was evaporated to dryness under reduced pressure. After dissolution of the residue in 10 ml of ethanol 1 equivalent of hydrochloric acid in ethanol was added. After dilution with 2 ml of ether the title compound was obtained with a melting-point of 234°-235° C.

EXAMPLE VI

4-Fluoro-N-[2-[4-{5-(2-hydroxymethyl-1,4-benzodioxanyl}-1-piperazinyl]ethyl]benzamide HCl.

6.36 Mmol (3,30 g) of 4-fluoro-N-[2-[4-{5-(2-benzoyloxymethyl-1-piperazinyl]ethyl]benzamide oxymethyl-1,4-benzodioxanyl)}-1-piperazinyl]ethyl]benzamide were dissolved in 90 ml of ethanol. A solution of 6.36 mmol (0.36 g) of potassium hydroxide in 10 ml of water was added at once. After stirring at room temperature for 15 hours, the reaction mixture was evaporated to dryness under reduced pressure (40° C). The resulting residue was dissolved in methylene chloride (50 ml) and washed successively with water (50 ml) and a 5% sodium bicarbonate solution (50 ml). The organic layer was dried on magnesium sulfate and then evaporated to dryness under reduced pressure. 1 Equivalent of alcoholic hydrochloric acid was added to the residue dissolved in 15 ml of dry ethanol. After dilution with 40 ml of ether, the title compound was obtained with a melting-point of 187°-188° C.

The following compounds were prepared from the said starting compounds in an analogous manner:

2. 4-fluoro-N-[2-[4-{5-(3-hydroxymethyl-1,4-benzodioxanyl)}-1-piperazinyl]ethyl]benzamide HCl, melting-point 186.5°-187.5° C. (ethanol/ether 1:3) from 4-fluoro-N-[2-[4-{5-(3-benzoyloxymethyl-1,4-benzodioxanyl}-1-piperazinyl]ethyl]benzamide and potassium hydroxide;

3. (+)-4-fluoro-N-[2-[4{5-(2-hydroxymethyl-1-benzodioxanyl)}-1-piperazinyl]ethyl]benzamide HCl, melting-point 184.5°-185.5° C. from (+)-4-fluoro-N-[2-[4-{5-(2-benzoyloxymethyl-1,4-benzodioxanyl)}-1-piperazinyl]ethyl]benzamide and potassium hydroxide;

4. 4-fluoro-N-[2-[4-{5-(2-hydroxyethyl-1,4-benzodioxanyl)}-1-piperazinyl]ethyl]benzamide HCl, melting-point 171.5°-172° C. from 4-fluoro-N-[2-[4-{5-(2-benzoyloxyethyl-1,4-benzodioxanyl)}-1-piperazinyl]ethyl]benzamide and potassium hydroxide;

5. 4-fluoro-N-[2-[4-{5-(2-(1-hydroxyethyl)-1,4-benzodioxanyl),}-1-piperazinyl]ethyl]benzamide HCl, melting-point 196°-197° C. from 4-fluoro-N-[2-[4-{5-(2-(1-benzoyloxyethyl-1,4-benzodioxanyl)}-1-piperazinyl]ethyl]benzamide and potassium hydroxide.

6. N-[2-[4-{5-(2-hydroxymethyl-1,4-benzodioxanyl)}-1-piperazinyl]ethyl]-2-thiophenecarboxamide HCl, melting-point 172°-174° C. (ethanol/ether 4:1) from N-[2-[4-{5-(2-(2-thiophenecarboxyloxymethyl)-1,4-benzodioxanyl)}-1-piperazinyl]ethyl]-2-thiophenecarboxamide and potassium hydroxide;

7. N-[2-[4-{5-(2-hydroxymethyl-1,4-benzodioxanyl)}-1-piperazinyl]ethyl]-2-furancarboxamide HCl, melting-point 200°-201° C. (ethanol) from N-[2-[4-{5-(2-(2-furancarboxyloxymethyl)-1,4-benzodioxayl)}-1-piperazinyl]ethyl]-2-furancarboxamide and potassium hydroxide;

8. N-[2-[4-{5-(2-hydroxymethyl-1,4-benzodioxanyl)}-1-piperazinyl]ethyl]-2-pyrrolecarboxamide 2HCl, melting-point 178° C. (dec.) (ethanol/ether 5:1) from N-[2-[4-{5-(2-(2-pyrrolecarboxyloxymethyl)-1,4-benzodioxanyl)}-1-piperazinyl]ethyl]-2-pyrrolecarboxamide and potassium hydroxide;

9. N-[2-[4-{5-(2-hydroxymethyl-1,4-benzodioxanyl)}-1-piperazinyl]ethyl]-2-pyrazinecarboxamide HCl, melting-point 170° C. (dec.) (ethanol/ether 5:1) from N-[2-[4-{5-(2-(2-pyrazinecarboxyloxymethyl)-1,4-benzodioxanyl)}- 1-piperazinyl]ethyl]-2-pyrazinecarboxamide and potassium hydroxide;

10. 4-nitro-N-[2-[4-{5-(2-hydroxymethyl-1,4-benzodioxanyl)}-1-piperazinyl]ethyl]benzamide 2HCl, melting-point 153°-156° C. (ethanol/ether 6:1) from 4-nitro-N-[2-[4-{5-(2-benzoyloxymethyl-1,4-benzodioxanyl)}-1-piperazinyl]ethyl]benzamide and potassium hydroxide;

11. 4-cyano-N-[2-[4-{5-(2-hydroxymethyl-1,4-benzodioxanyl)}-1-piperazinyl]ethyl]benzamide 2HCl, melting-point 149°-153° C. (ethanol/ether 5:1) from 4-cyano-N-[2-[4-{5-(2-benzoyloxymethyl-1,4-benzodioxanyl)}-1-piperazinyl]ethyl]benzamide and potassium hydroxide;

12. 2-fluoro-N-[2-[4-{5-(2-hydroxymethyl-1,4-benzodioxanyl)}-1-piperazinyl]ethyl]benzamide 2HCl, melting-point 195°-199° C. (ethanol) from 2-fluoro-N-[2-[4-{5-(2-benzoyloxymethyl-1,4-benzodioxanyl}-1-piperazinyl]ethyl]benzamide and potassium hydroxide;

13. 3-fluoro-N-[2-[4-{5-(2-hydroxymethyl-1,4-benzodioxanyl)}-1-piperazinyl]ethyl]benzamide 2HCl, melting-point 171° C.(dec.) (ethanol/ether 5:1) from 3-fluoro-N-[2-[4-{5-(2-benzoyloxymethyl-1,4-benzodioxanyl)}-1-piperazinyl]ethyl]benzamide and potassium hydroxide;

14. 2,4-difluoro-N-[2-[4-{5-(2-hydroxymethyl-1,4-benzodioxanyl)}-1-piperazinyl]ethyl]benzamide 2HCl, melting-point 201°-204° C. (ethanol/ether 5:1) from 2,4-difluoro-N-[2-[4-{5-(2-benzoyloxymethyl-1,4-benzodioxanyl)}-1-piperazinyl]ethyl]benzamide and potassium hydroxide;

EXAMPLE VII

4-Fluoro-N-[2-[4-{5-(2-benzoyloxymethyl-1,4-benzodioxanyl}-1-piperazinyl]ethyl]benzamide HCl.

3.5 Mmol (1.45 g) of 4-fluoro-N-[2-[4-{5-(2-hydroxymethyl-1,4-benzodioxanyl)}-1-piperazinyl]ethyl]benzamide and 4.3 mmol (0.43 g) of triethyl amine were dissolved in 30 ml of dry tetrahydrofuran. While cooling with ice, a solution of 4.3 mmol (0.60 g) of benzoyl chloride in 25 ml of tetrahydrofuran was added in 10 minutes. Refluxing was carried out for 24 hours and, after cooling to room temperature, 50 ml of ether were added after which the solution was washed with 50 ml of water, 10 ml of 2 N sodium hydroxide solution and 50 ml of water. After drying on magnesium sulfate, the organic layer was evaporated to dryness in vacuo. The residue was chromatographed over silicagel using ethyl acetate as an eluent. The free base thus obtained was dissolved in 25 ml of ethanol and 1 equivalent of nydrochloric acid in ethanol was added. The clear solution was concentrated in vacuo to 15 ml and, after the addition of 8 ml of ether, the title compound was obtained with a melting-point of 210°-211° C.

The following compound was prepared in an analogous manner from the said starting compounds:

2. 4-fluoro-N-[2-[4-{5-(2-dimethyl-1-oxopropyloxymethyl)-1,4-benzodioxanyl)}-1-piperazinyl]ethyl]benzamide HCl, melting point 197°-200° C. from 4-fluoro-N-[2-[4-{5-(2-hydroxymethyl-1,4-benzodioxanyl)}-1-piperazinyl]ethyl]benzamide and 2,2-dimethylpropionyl chloride

EXAMPLE VIII

4-Fluoro-N-[2-[4-{8-(2,3-dihydro-1,4-benzoxazinyl)}-1-piperazinyl]ethyl]benzamide.

2 Mmol (0.85 g) of 4-fluoro-N-[2-[4-{8-(4-acetyl-2,3-diohydro-1,4-benzoxazinyl)}-1-piperazinyl]ethyl]benzamide were dissolved in 20 ml of methanol, after which 20 ml of 2 N hydrochloric acid were added. After refluxing for 1 hour, the mixture was cooled to 5° C. after which 25 ml of 2 N sodium hydroxide were added. The mixture was then extracted with 4×25 ml of methylene chloride. The resulting organic layer was washed with brine solution, dried on magnesium sulfate and evaporated to dryness under reduced pressure. The residue was crystallized from 5 ml of ethanol giving, the title compound having a melting-point of 148°–150° C. being obtained.

EXAMPLE IX

4-Fluoro-N-[2-[4-{5-(2-acetyl-1,4-benzodioxanyl)}-1-piperazinyl]ethyl]benzamide HCl.

0.57 Mmol (0.27 g) of 4-fluoro-N-[2-[4-{5-(2-(1-(1,3-ethylenedioxy)ethyl)-1,4-benzodioxanyl)}-1-piperazinyl]ethyl]benzamide were dissolved in 5 ml of dioxane. After the addition of 5 ml of 2N hydrochloric acid, the mixture was heated at 100° C. for 41 hours. After concentrating the reaction mixture under reduced pressure to approximately 4 ml, 6 ml of 2N sodium hydroxide were added, after which extraction was carried out with 4×10 ml of methylene chloride. The organic layer was dried on sodium sulfate and evaporated to dryness under reduced pressure. The resulting residue was chromatographed over silicagel with a mixture of methylene chloride and methanol (9/1) as the eluent. The resulting free base was dissolved in 2 ml of ethanol and converted into the hydrochloride with 1 equivalent of hydrochloric acid.

EXAMPLE X

4-Fluoro-N-[2-[4-{4-(2-ethylene-1,3-benzodioxolyl)}-1-piperazinyl]ethyl]benzamide.

4.34 Mmol (2.47 g) of 4-fluoro-N-[2-4-{5-(2-(4-methylphenyl)sulfonyloxymethyl-1,4-benzodioxanyl)}-1-piperazinyl]ethyl]benzamide were dissolved in 25 ml of pyridine and refluxed for 90 hours under an atmosphere of nitrogen. The reaction mixture was evaporated to dryness under reduced pressure. The residue was taken up in 30 ml of methylene chloride and the solution was washed with 2×15 ml of 2 N sodium hydroxide and 2×20 ml of water. The organic layer was evaporated to dryness under reduced pressure and the resulting residue was chromatographed over silicagel with methylene chloride-methanol (3%) as an eluent. The free base obtained in this manner was crystallized from 2 ml of ethyl acetate +0.5 ml of petroleum ether, the title compound having a melting-point of 152.5°–153° C. being obtained.

EXAMPLE XI

4-Fluoro-N-[2-[4-{4-(2-phenylbenzimidazolyl)}-1-piperazinyl]ethyl]benzamide, 2HCl.

5.88 Mmol (2.1 g) of 4-fluoro-N-[2-{4-(2,3-diaminophenyl)-1-piperazinyl}ethyl]benzamide were dissolved in 50 ml of ethanol. 6,5. Mmol (1.2 g) of ethyl iminobenzoate hydrochloride were added in one portion. The mixture was heated for 3 hours at 90° C., and then the solution was evaporated to dryness under reduced pressure. The residue was taken up in 100 ml of methylene chloride, and the solution was washed twice with 20 ml of water. The organic layer was evaporated to dryness under reduced pressure, and the so obtained residue was chromatographed over silicagel with ethyl acetate as eluent. The so obtained free base was dissolved in ethanol and 2 equivalents of hydrochloric acid were added to this solution. After dilution with ethyl acetate the title compound was obtained having a melting point of 230°–232° C.

The following compounds were prepared from the indicated starting materials in an analogous manner.

2. 4-fluoro-N-[2-[4-{4-(2-methylbenzimidazolyl)}-1-piperazinyl]ethyl]benzamide 2HCl; melting-point 100° C. (decomposition), ethanol/methyl ethyl ketone 1:1) from 4-fluoro-N-[2-{4-(2,3-diaminophenyl)-1-piperazinyl)}-ethyl]benzamide and ethyl iminoacetate;

3. 4-fluoro-N-[2-{4-(4-benzimidazolyl)-1-piperazinyl}-ethyl]benzamide di-maleate; melting-point 154.5°–162° C. (decomposition), (ethanol) from 4-fluoro-N-[2-{4-(2,3-diaminophenyl)-1-piperazinyl{ethyl]benzamide and formic acid.

EXAMPLE XII

4-Fluoro-N-[2-{4-(2-benzimidazolinon-4-yl)-1-piperazinyl}ethyl]benzamide.

10 Mmol (3.57 g) of 4-fluoro-N-[2-{4-(2,3-diaminophenyl)-1-piperazinyl}ethyl]benzamide were dissolved in 35 ml of tetrahydrofuran (which had been distilled over LiAlH$_4$), and the solution was cooled in an ice-bath to 0° C. under an atmosphere of nitrogen. 21 Mmol (3.4 g) of 1,1'-carbonyldiimidazole in 20 ml of tetrahydrofuran was added in one portion to this solution while vigorously stirring. The temperature raised to 10° C. Thereafter the mixture was stirred for 3 hours at room temperature. The reaction mixture was evaporated to dryness under reduced pressure, the residue was taken up into chloroform, and the solution was washed with water. The organic layer was evaporated to dryness, and the residue was chromatographed over silicagel with a mixture of methylene chloride, methanol and 25% of ammonia (92:7.5:0.5) as the eluent. The so obtained base was cyrstallized from ethanol, and the title compound was obtained having a melting-point of 240°–243.5° C.

EXAMPLE XIII

4-Fluoro-N-[2-{4-(4-benzotriazolyl)-1-piperazinyl}ethyl]-benzamide.

6.7 Mmol (2.9 g) of 4-fluoro-N-[2-)4-(2,3-diaminophenyl)-1-piperazinyl(ethyl)benzamide dihydrochloride were dissolved in 67 ml of 0.5 N HCl. 7 Mmol (0.48 g) of sodium nitrite dissolved in 10 ml of water were added to the solution in one portion after which the mixture was stirred for 2 hours at room temperature. Then the solution was neutralized with sodium bicarbonate, followed by extraction with chloroform. The organic layer was evaporated to dryness under reduced pressure, and the residue was chromatographed over silicagel with a mixture of methylene chloride, methanol and 25% of ammonia (92:7.5:2.5) as the eluent. The so obtained free base was crystallized from a mixture of ethanol, ether and petroleum ether (1:8:5), giving the title compound with a melting-point of 221°–225° C.

The following compound has been prepared in an analogous manner from the indicated starting compounds: 4-fluoro-N-[3-[4-(4-benzotriazolyl)-1- piperazinyl]propyl]benzamide (melting point 204°–205° C.) from 4-fluoro-N-[3-[4-(2,3-diaminophenyl)-1-piperazinyl]propyl]benzamide.

EXAMPLE XIV

4-Fluoro-N-[2-[4-{5-(2-methylene-1,4-benzodioxanyl)}-1-piperazinyl]ethyl]benzamide.

39.74 Mmol of potassium was dissolved in 190 ml of tert. butanol while heating at 100° C. and under an atmosphere of nitrogen. The solution was cooled to 60° C., and at this temperature 26.36 mmol (15.0 g) of 4-fluoro-N-[2-[4-{-5-(2-(4-methylphenyl)sulfonyloxymethyl-1,4-benzodioxanyl)}-1-piperazinyl]ethyl]benzamide were added. Then the mixture was heated for 4 hours at 100° C. 300 Ml of water were added to the cooled reaction mixture, and this was stirred for half an hour at room temperature. The solid substance was filtered, washed with water, and dried over pellets of potassium hydroxide at 50° C., under reduced pressure (5 mm Hg). After crystallization from toluene the title compound was obtained with a melting-point of 181°–184° C.

EXAMPLE XV

1-[5-(1,4-benzodioxanyl)]piperazine HCl.

128 Mmol (23,9 g) of 5-amino-1,4-bendioxan HCl and 140 mmol (25,0 g) of of bis-(2-chloroethyl)amine HCl were suspended in 250 ml of chlorobenzene. The mixture was heated for 66 hours at 130° C. while stirring. The reaction mixture was cooled to 90° C. and diluted with 200 ml of ethyl acetate. The solid substance was filtered off and washed with ethyl acetate. The crude compound was stirred in 600 ml of absolute ethanol, and then the precipitate was dissolved in 600 ml of warm absolute ethanol and 75 ml of 96% ethanol. After distilling off about 150 ml of liquid the solution was cooled while stirring, after which 23,1 g of the title compound having a melting-point of 256°–258° C. was obtained.

In analogous manner other compounds of the formula 22 used as staring materials in the above Examples have been prepared.

I claim:
1. Blood-pressure lowering compounds of the formula

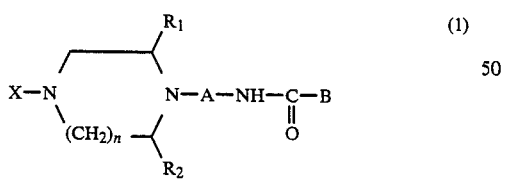

(1)

wherein $R_1$ and $R_2$ independently of each other represent hydrogen or an alkyl group having 1–3 carbon atoms, n has the value 1 or 2, X is a group selected from the group consisting of

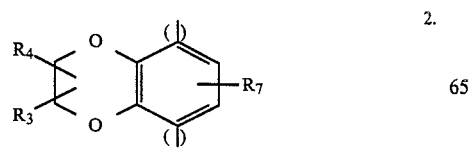

2.

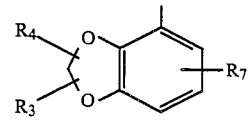

3.

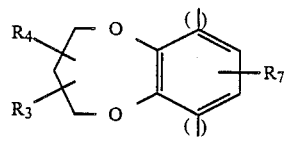

4.

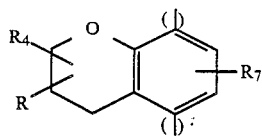

5.

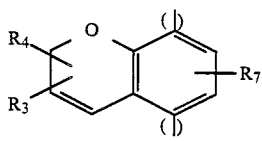

6.

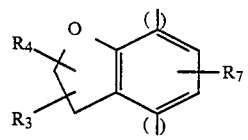

7.

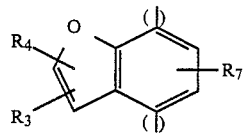

8.

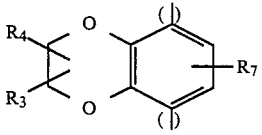

9.

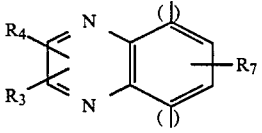

10.

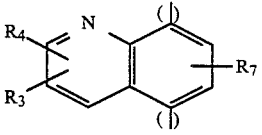

11.

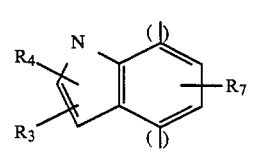

12.

-continued

13. 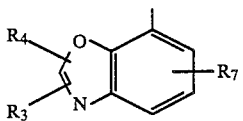

14. 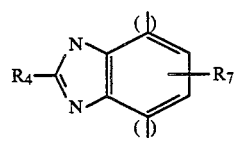

15. 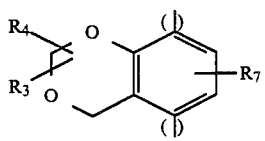

16. 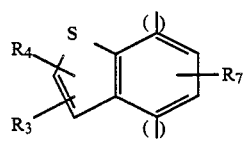

17. 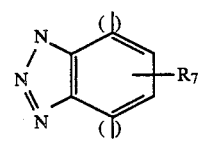

18. 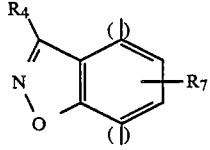

19. 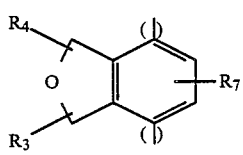

20. 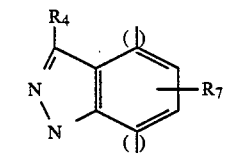

21. 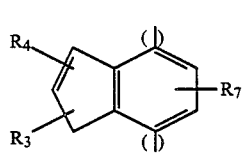

22. 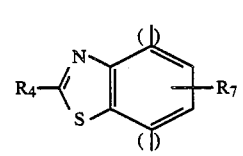

wherein the groups of the formulae 2, 5, 6, 9, 10, 11 and 15 are linked on position 5 or 8, the group of formula 4 is linked on position 6 or 9, and the groups of formulae 7, 8, 12, 13, 14 and 16–22 are linked on position 4 or 7 to the nitrogen atom of the piperazine group, and wherein $R_3$ is hydrogen or straight or branched alkyl having 1–3 carbon atoms, $R_4$ is hydrogen, halogen, alkyl having 1–3 carbon atoms, vinyl, straight or branched hydroxyalkyl having 1–3 carbon atoms, which may be etherified or esterified, alkyl carbonyl having 1–3 carton atoms in the straight or branched alkyl group, or a phenyl group, $R_7$ is hydrogen or fluoro, A is a straight or branched alkylene chain having 2–10 carbon atoms, B is a phenyl or phenyl substituted with 1 or 2 halogen atoms, a cyano group, a nitro group or a straight or branched alkyl group having 1–3 carbon atoms, or B is a saturated or unsaturated cycloalkyl group having 4–8 carbon atoms, or B is a heterocyclic radical selected from the group consisting of 23. 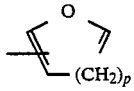

24. 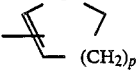

25. 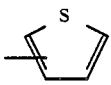

26. 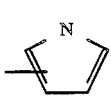

27. 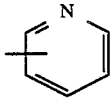

28. 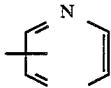

wherein p has the value 1 or 2, and the salts thereof with pharmaceuticvally acceptable acids.

2. Compounds as claimed in claim 1, of formula 1, wherein

X is the group of formula 2, $R_3$ is hydrogen, $R_4$ is hydrogen, hydroxymethyl or esterified hydroxymethyl, $R_7$ is hydrogen or fluoro, n=1

$R_1$ and $R_2$ are hydrogen,

A is a straight or branched alkylene chain having 2–10 carbon atoms, and

B is a phenyl or 4-fluorophenyl.

3. 4-Fluoro-N-2-{4-{5-(2-hydroxymethyl-1,4-benzodioxzanyl)]-1-piperazinyl}ethyl]benzamide and the salts thereof with pharmaceutically acceptable acids.

4. (+)-4-Fluoro-N-[2-{4-[5-(2-hydroxymethyl-1,4-benzodioxanyl)]-1-piperazinyl}ethyl]benzamide and the salts thereof with pharmaceutically acceptable acids.

5. 4-Fluoro-N-[2-{4-[5-{2-(2,2-dimethyl-1-oxo-propyloxymethyl-1,4-benzodioxanyl)}-1-piperazinyl}ethyl)-benzamide and the salts thereof with pharmaceutically acceptable acids.

6. N-[2-methyl-2-{4-[5-(1,4-benzodioxanyl)]-1-piperazinyl}ethyl]cyclohexane carbonamide and the salts thereof with pharmaceutically acceptable acids.

7. (+)-4-fluoro-N-[3-[4-[5-(2-hydroxymethyl-1,4-benzodioxanyl)]-1-piperazinyl]propyl]benzamide.

8. (+)-4-fluoro-N-[4-[4-[5-(2-hydroxymethyl-1,4-benzodioxanyl)]-1-piperazinyl]butyl]benzamide.

9. 4-fluoro-N-[3-[4-[7-(2-hydroxybenzoxazolyl)]-1-piperazinyl]propyl]benzamide.

10. 4-fluoro-N-[3-[4-(4-benzotriazolyl)-1-piperazinyl]-propyl]benzamide.

11. Compositions having blood-pressure lwering activity, characterized in that an effective amount of at least one compound of claim 11 is present therein as an active component in a pharmaceutically acceptable carrier therefor.

12. A method of lowering blood-pressure, characterized in that a composition as claimed in claim 11 is used.

* * * * *